United States Patent [19]

Maeda

[11] Patent Number: 4,604,999
[45] Date of Patent: Aug. 12, 1986

[54] INHALATOR

[75] Inventor: Masatoshi Maeda, Hikoni, Japan

[73] Assignee: Matsushita Electric Works, Ltd., Osaka, Japan

[21] Appl. No.: 603,427

[22] Filed: Apr. 24, 1984

[30] Foreign Application Priority Data

May 14, 1983 [JP] Japan .................................. 58-84372

[51] Int. Cl.⁴ ............................................ A61M 15/00
[52] U.S. Cl. ............................ 128/200.21; 128/203.17; 604/335
[58] Field of Search ........................ 128/200.14, 200.18, 128/200.21, 200.19, 203.16, 203.17, 203.26, 203.27, 368; 604/335; 137/614.04

[56] References Cited

U.S. PATENT DOCUMENTS

| 1,756,053 | 4/1930 | Colton | 128/203.27 |
| 2,576,110 | 11/1951 | Fisher | 128/203.17 |
| 3,742,629 | 7/1973 | Plasko | . |
| 3,972,387 | 8/1976 | Braun | 137/614.04 |
| 4,058,120 | 11/1977 | Caparrelli et al. | 137/614.04 |
| 4,463,248 | 7/1984 | Katzman et al. | 128/203.17 |

FOREIGN PATENT DOCUMENTS 54-5342 3/1979 Japan .

Primary Examiner—Henry J. Recla
Attorney, Agent, or Firm—Burns, Doane, Swecker & Mathis

[57] ABSTRACT

An inhalator comprises a water level adjusting chamber which fluidly communicates a water supply chamber and a vaporizing chamber. A manually operable valve interrupts communication between the level adjusting and vaporizing chambers. Upon closing of the valve, a power supply circuit is turned on to energize a heater for heating water in the vaporizing chamber. The interruption of communication between the level adjusting and vaporizing chambers during the use is effective to obtain only a relatively small amount of water to be heated.

5 Claims, 4 Drawing Figures

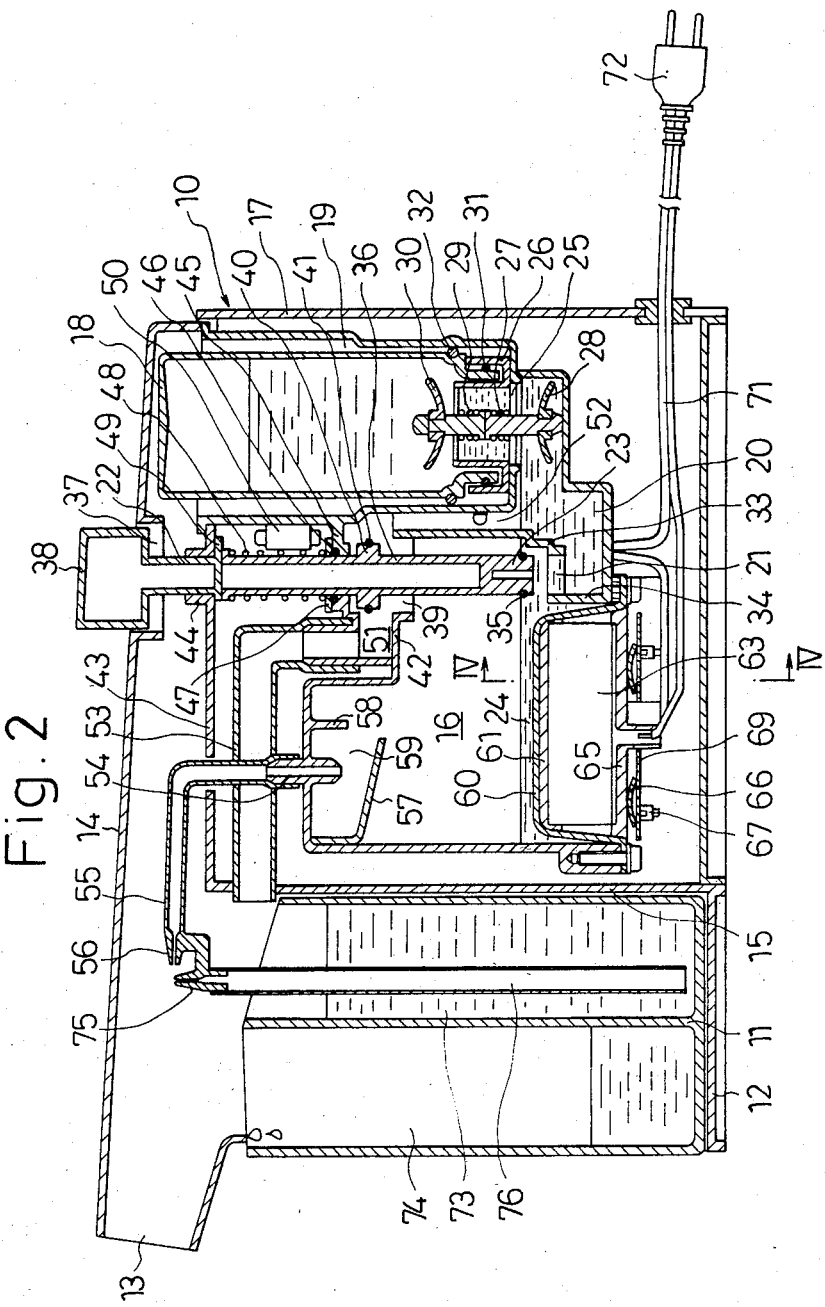

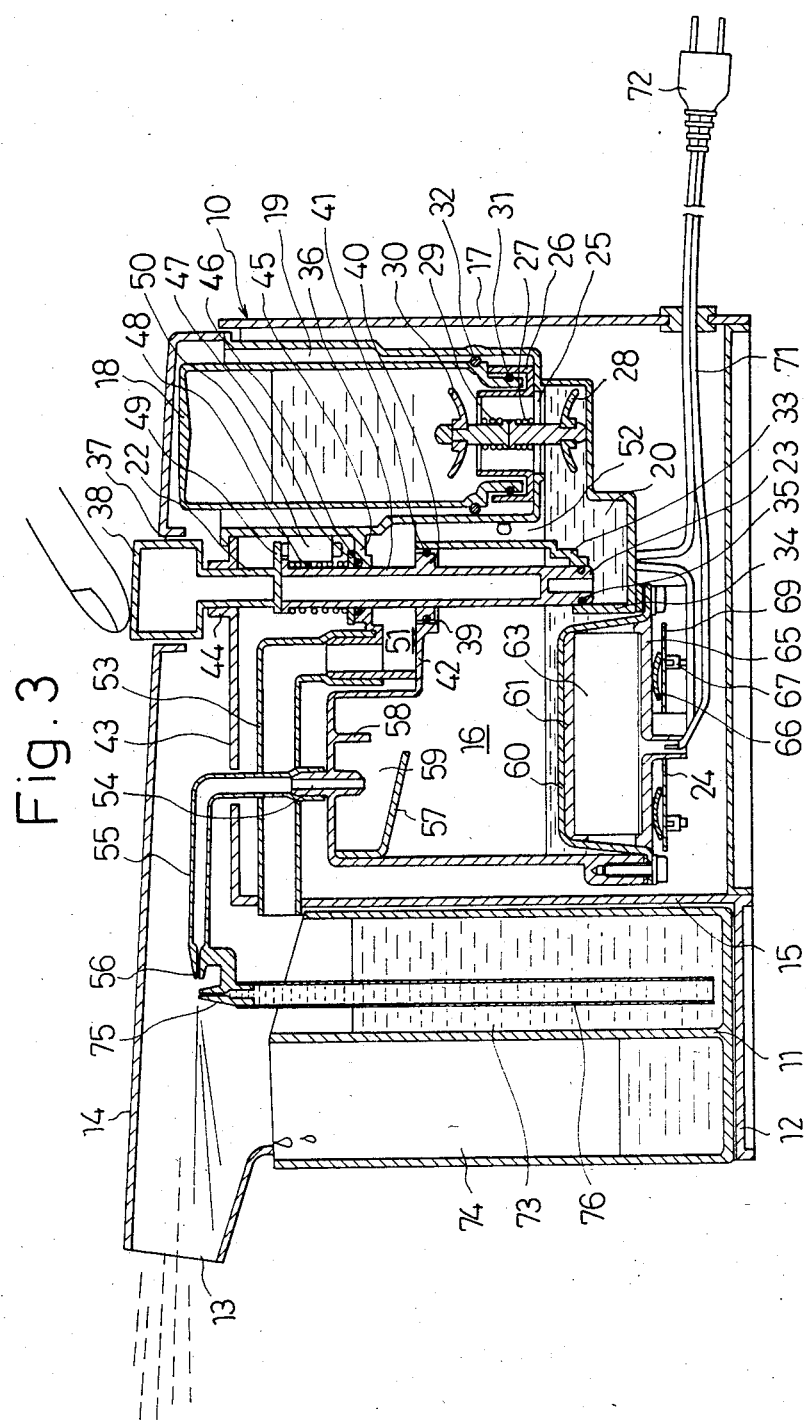

INHALATOR

BACKGROUND ART

This invention relates to inhalators in which water in a vaporizing chamber is boiled by a heater to generate vapor and, more specifically, improvements in the inhalators the ejection of generated vapor of which causes a medicinal liquid or the like inhalant contained in a suction tank sucked up and atomized for inhalation into patient's mouth to lessen his throat pain and the like.

Although not used as the inhalator, there has been suggested a steamer for generating vapor using a heater in U.S. Pat. No. 3,742,629 of E. R. Plasko dated July 3, 1973 or Japanese Patent Publication No. JP, B, 5342/1979 of S. Takakuwa et al dated Mar. 15, 1979. In the steamer of the former patent, a vapor tank of truncated conical shape is made relatively small, a nozzle is secured as extending obliquely upward at the head portion of the tank and a heater assembly is vertically erected within the tank. This steamer, however, has a problem that, because the tank is made small, water in the tank can be soon used up and thus the user must frequently supplement water into the tank every time of use. In addition, since the water supplementation is performed usually manually and it is difficult to maintain always constant the amount of supplemented water, the time required for vapor generation determined by the supplemented water amount is made variable and the time of continuous use available for each water supplementation is also made variable, so that there have been various difficulties in its practical applications.

On the other hand, in the steamer of the latter publication, a vaporizing chamber having a heater secured thereto and a water reservoir chamber are provided. The top end portion of a water pipe is coupled through a valve means to the water reservoir chamber. The pipe extends between the vaporizing and reservoir chambers and is projected downward into the vaporizing chamber. The water pipe is provided at its downward tip end with a small hole and at the circumference above the tip end with water outflow holes so as to determine the level of water supplied into the vaporizing chamber. This arrangement is advantageous in that the water level in the vaporizing chamber is determined by the water outflow holes of the water pipe and thus the time necessary for vapor generation is made constant, and that water can be continuously supplied from the water reservoir to the vaporizing chamber and thus the continuous operation time can be prolonged sufficiently, removing various problems occurred in the above U.S. Patent. However, this arrangement is still defective in that when the water level within the vaporizing chamber temporarily drops below the outflow holes of the water pipe, the amount of ejected vapor is decreased, i.e., the vapor ejection pressure is not constant but is rather varied. Therefore, this arrangement is completely unsuitable for use as the inhalator which utilizes the vapor ejection pressure to suck and atomize the inhalant from a suction tank by the Venturi effect.

In the arrangement of Japanese Patent Publication, further, the small hole provided in the tip end of the water pipe is open in the vaporizing chamber, so that the heated water may be subject to inherent convection through this hole, making impossible to realize a rapid vapor generation. In this connection, if the small hole is selected to have such a diameter that can prevent the convection, then the small hole is clogged by fur and the like and its function of adjusting the supplied water level is disadvantageously lost.

TECHNICAL FIELD

A primary object of the present invention is, therefore, to provide an inhalator for the ejection of generated vapor of boiled water in a vaporizing chamber to suck and atomize the inhalant from a suction tank, which enables a continuous supply of a fixedly small amount of water for a long time, achievement of rapid vapor generation and retention of substantially constant vapor ejection, to assure the satisfactory Venturi effect.

This object of the present invention is attained specifically by arranging the inhalator to have a water level adjusting chamber between the vaporizing chamber and a water supply chamber containing a detachable water supply tank for keeping a constant water level in the vaporizing chamber, and a valve means between the vaporizing chamber and the water level adjusting chamber for interrupting communication between them upon use of the inhalator. With this arrangement, the supplied water level in the vaporizing chamber is kept at a level determined by the water level adjusting chamber and, when the inhalator is used, the communication between the vaporizing and adjusting chambers is interrupted, preventing the occurrence of convection during heating of water, whereby the above object can be effectively realized.

Other objects and advantages of the present invention shall become clear from the following description of the invention detailed with reference to an embodiment illustrated in accompanying drawings.

BRIEF EXPLANATION OF THE DRAWINGS

FIG. 2 is a vertical cross-sectional view showing the interior structure of the inhalator taken along line II—II in FIG. 1, in its non-operating state;

FIG. 3 is similar vertical cross-sectional view to FIG. 2 except that the valve means is in its operating position.

Figure 1:
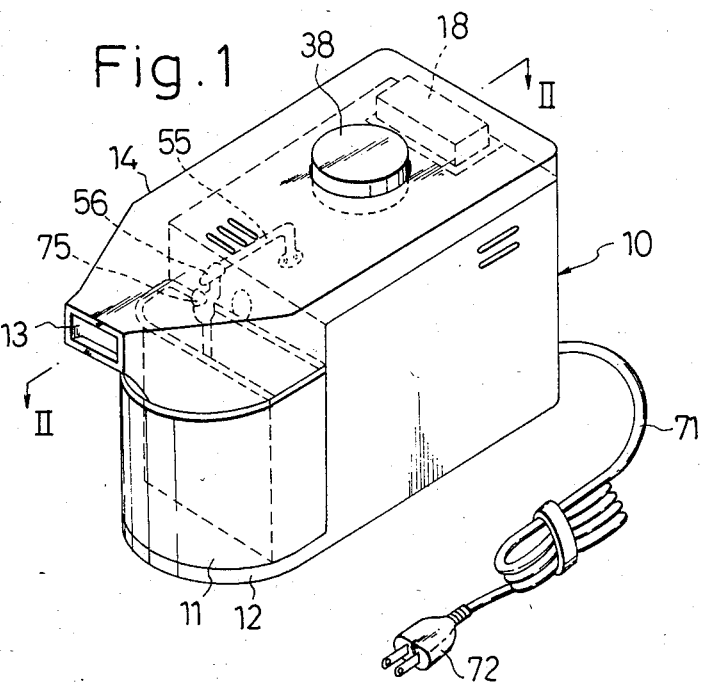
FIG. 1 is a perspective view showing an overall inhalator according to the present invention.

While the present invention shall now be described with reference to a preferred embodiment shown in the drawings, it should be understood that the intention is not to limit the invention only to the particular embodiment shown but rather to cover all alterations, modifications and equivalent arrangements possible within the scope of appended claims.

DISCLOSURE OF THE INVENTION

Referring to FIGS. 1 and 2, there is shown an inhalator according to the present invention which generally comprises a housing 10, a suction tank 11 containing an inhalant liquid such as a salt solution and the like, and a skirt 12 projected out of the front part of the housing 10 and carrying the suction tank 11, and a cover 14 having an ejected vapor outlet 13 forwardly and substantially horizontally extended and covering the upper side of the housing. The housing 10 and cover 14 together define a casing. In this case, it is preferable that the housing 10, suction tank 11 and cover 14 are all made of a heat resistant synthetic resin. Within the housing 10, a vaporizing chamber 16 is provided behind a front wall 15 of the housing 10, and a water supply chamber 19 detachably accommodating therein a water supply tank 18 is provided in the vicinity of a back wall 17 of the housing. The water supply tank 18 is preferably made of a heat-resistant transparent synthetic resin such as polycarbonate. In the illustrated embodiment, the water supply chamber 19 is positioned at a level higher than the vaporizing chamber 16, and a water level adjusting chamber 20 which functions to maintain the level of water in the chamber 16 constant is disposed between the vaporizing and water supply chambers 16 and 19. In addition, a vertically movable valve member 22 made desirably of a heat resistant synthetic resin is disposed vertically above an upwardly opened communication path 21 between the vaporizing chamber 16 and the water level adjusting chamber 20 so that lower end portion 23 of the valve member 22 normally biased upward can engage in the path 21 to close it. A heater means 24 is disposed in the bottom part of the vaporizing chamber 16.

Referring more in detail to the arrangement of the respective parts of the above inhalator, the water supply chamber 19 is formed to have at its bottom a water supply port 25, and a water supply valve 28 is movably provided in this water supply port 25 so as to normally close the port 25 as so biased by means of a spring 27. The water supply tank 18 has, on the other hand, at the top port of its bottle shape a cap 26 removably mounted to the port through a sealing O-ring 31 and carrying a valve 30 movably provided in a central opening of the cap 26 so as to normally close the opening as so biased by a spring 29. When the user places the water supply tank 18 filled with water into the water supply chamber 19, turning the tank upside down, to have the cap 26 seated on the bottom of the chamber 19 in alignment with the port 25, a projected rod of the valve 28 abuts against a projected rod of the valve 30 of the tank 18, compressing the respective springs 27 and 29 to each other, whereby the both valves 28 and 30 are caused to shift into their position of opening the water supply port 25 and the port of the tank 18, so as to supply water of the tank 18 into the water level adjusting chamber 20. In this case, a sealing O-ring 32 fitted around the tank 18 adjacent the top port resiliently engages with the inner peripheral wall of the chamber 19 to achieve a water-tight sealing around the water supply port 25.

In the illustrated embodiment, the water level adjusting chamber 20 is arranged to have a two-stage stepped bottom and its upper stage surface acts as a stopper for the downward shift of the valve 28 to keep the valve 30 of the tank 18 in its opening position. The water level adjusting chamber 20 communicates with the vaporizing chamber 16 through the communication port 21 opened upward in the lower stage bottom part as defined by opposing inner wall portions 33 and 34 of the housing 10. The valve member 22 is of a vertically elongated rod shape, the lower end portion 23 of which having a sealing O-ring 35 fitted therearound can be sealingly inserted into the communication path 21 when depressed downward against the upward biasing force to interrupt the communication. The valve member 22 thus comprises an elongated valve rod 36 having the lower end portion 23 and a push-button 38 integrally secured to the other top end of the rod for upward projection out of an opening 37 of the cover 14. This valve rod 36 extends through a vapor-release vent 39 of the chamber 16 opened above the communication path 21, and a closure flange 40 provided at an intermediate position of the rod 36 is sealingly engaged into the vent 39 upon the downward depression, so that a sealing O-ring 41 fitted to the outer periphery of the flange 40 will fluid-tightly engage with the upper end of the inner wall portion 33 and opposing end portion of upper wall portion 42 of the chamber 16 which are defining the vent 39. As a result, when the valve rod 36 is shifted downward with the push button 38 depressed, the communication path 21 and vapor release vent 39 are both closed concurrently.

The valve rod 36 is slidably guided by a lip portion 44 projecting upwardly from the periphery of an opening of a horizontally extending upper wall 43 of the housing 10 and also by the peripheral edge of another opening of an inner wall portion 45 horizontally extended from the front side wall of the water supply chamber 19 in the housing 10. In the illustrated embodiment, a sealing O-ring 46 is fitted to the peripheral edge of the opening in the inner wall portion 45. A sealing plate 47 having an opening through which the valve rod 36 is slidably passed is disposed above the O-ring 46, and a return coil spring 48 is fitted around the rod 36 between the sealing plate 47 and an upper flange having a rearwardly extended actuating arm 49 of the rod 36 at a position just below the lip portion 44 of the housing 10, so that the rod 36 is normally biased into its upper position of FIG. 2, while the plate 47 is biased always against the O-ring 46 to sufficiently achieve fluid-tight sealing at the opening of the inner wall portion 45. A microswitch 50 is mounted to the front side wall of the water supply chamber 19 to be actuated by the arm 49 of the valve rod 36 upon its downward movement so that the microswitch 50 electrically connected to a circuit for energizing the heater means 24 will cause an electric current to be fed to the heater means 24 as a result of the depression of the push button 38.

A vapor release space 51 is defined by the inner wall portion 42 having the vapor release vent 39 and the inner wall portion 45 extending above the vent 39 from the water supply chamber 19, and this space 51 communicates on its rear side with a vent passage 52 defined between the inner wall portion 33 of the vaporizing chamber 16 and the front wall portion of the water supply chamber 19, and on the front side with a vapor release duct 53 disposed above the vapor chamberizing 16 and opened at the front wall 15 of the housing 10. The duct 53 is preferably made of a heat-resistant synthetic resin. With this arrangement and at the upper position of the valve rod 36 as in FIG. 2, vapor present within the vaporizing chamber 16 can be discharged out of the housing 10 through the vapor release space 51 and duct 53 because the closure flange 40 is released from the vapor release vent 39. On the other hand, the water level adjusting chamber 20 is always subjected to the atmospheric pressure imparted through the duct 53, space 51 and vent passage 52. In addition, the vaporizing chamber 16 is provided at its top wall with a vapor outlet passage 54 of a tubular shape projected out of the top wall, and the passage 54 is coupled at projected end to a lower end of a vapor ejecting pipe 55 which is L-shaped and extended at the other upper end horizontally forwardly. The pipe 55 is desirably made of stainless steel or a heat-resistant synthetic resin and is provided at its upper end with an ejecting nozzle 56. The other inner end of the vapor outlet passage 54 is extruded into an outflow channel 59 defined by blocking plates 57 and 58 for preventing any condensed vapor droplet from entering directly into the passage 54.

Figure 4:
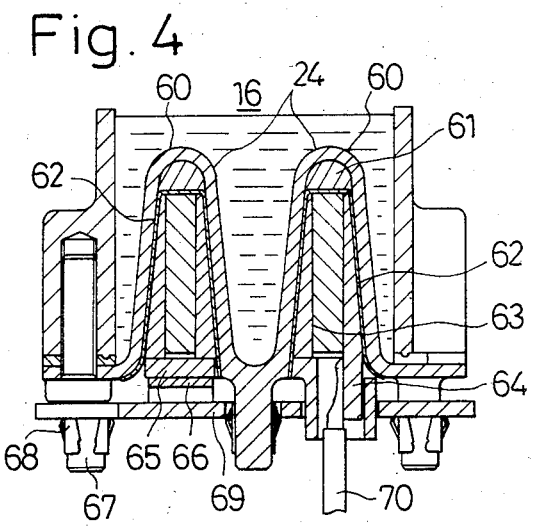
FIG. 4 is a vertical cross-sectional view as magnified of a heater means employed in the inhalator of FIGS. 1 through 3 but as seen on a plane rotated 90 degrees from that of FIG. 2.

Referring also to FIG. 4, the heater means 24 disposed at the bottom of the vaporizing chamber 16 comprises a heat radiating plate 60 secured to the lower end portions of inner walls of the vaporizing chamber 16 by screws or other proper securing means. In the present instance, the heat radiating plate 60 is preferably made of a zinc or aluminum die cast having a wavy shape in section including continuous two substantially inverted U-shaped portions slightly widened outward, inside the top of each of which portions a spacer 61 is provided, and an electrically insulating sheet 62 is provided against inner surfaces of the respective inverted U-shaped portions and of the spacers 61. The inverted U-shaped portions contain respectively a plate-shaped heat generating element 63 erected in width direction in the present instance to extend from the bottom of the inverted U-shaped portion to the lower surface of the spacer 61, as held between a pair of electrode plates 64 which are tapered toward the top of the inverted U-shaped portion to substantially fully conform to the inner side surfaces of the latter. The element 63 is made preferably of a thermistor having a positive characteristic. The electrode plates 64 are made of brass and the electrically insulating sheet 62 is made of a highly heat conductive silicon rubber, preferably. In the illustrated arrangement, the electrode plates 64 holding each of the heat generating elements 63 are thus electrically insulated by the sheet 62 from water inside the chamber 16.

A push-plate 65 is provided on the bottom end portions of the thus assembled heat generating elements 63 and electrode plates 64, and a bent-plate spring 66 is placed beneath the push-plate 65 for urging the assembled members 63 and 64 into the fully engaging position with the surrounding members 60–62, as carried by a support plate 69 secured by push nuts 68 to holding projections 67 formed integral with the heat radiating plate 60 and extended downward. That is, the push-plates 65 are pushed up by the spring 66 so that the electrode plates 64 come into tight contact with the heating element 63 by a wedge action occurring between the tapered outer surfaces of the electrode plates 64 and the inner side surfaces of the insulating sheet 62 within the inverted U-shaped portions of the wavy plate 60. The electrode plates 64 are connected through leading terminals 70 (only one of which is shown in FIG. 4) to a power supply cord 71 including the microswitch 50 and further through a plug 72 to a commerical power source.

The suction tank 11 mounted on the skirt portion 12 is divided into an inhalant chamber 73 on its rear side and a reservoir chamber 74 on its front side, and the reservoir chamber 74 is opened at its top to accommodate a lower wall end of the vapor outlet 13 positioned above the chamber 74. Disposed above also opened top of the inhalant chamber 73 is a suction nozzle 75 formed integral with the vapor nozzle 56 at right angled relation thereto, so as to perform the Venturi action when vapor is jetted from the nozzle 56, for which purpose the suction nozzle 75 is coupled to a suction tube 76 reaching nearly to the bottom of the inhalant chamber 73, the tube being also made preferably of a silicon rubber.

The operation of the inhalator according to the present invention shall be explained next. With the state shown in FIG. 1 of the device, the user removes the cover 14 and inserts the water-filled tank 18 into the water supply chamber 19 turning the tank upside down to seat the cap 26 on the bottom of the chamber 19 and thus to open the both valves 28 and 30. Then, water is supplied from the water supply tank 18 to the water level adjusting chamber 20 communicating with the water supply chamber 19 until air flowing into the water supply tank 18 through the duct 53, space 51 and vent passage 52 stops, that is, until the water level in the adjusting chamber 52 reaches the lower edge of the water supply port 25. Since the water level adjusting chamber 20 is positioned next to and substantially at the same level as the vaporizing chamber 16, it will be appreciated that water is also supplied into the chamber 16 to the same level as the chamber 20 communicating with each other, and this level is kept always constant so long as the communication between the chambers 16 and 20 is maintained.

Under this condition, when the user depresses the push button 38 with his finger from the position of FIG. 2 to shift the valve rod 36 to its lower position of FIG. 3, the lower end portion 23 of the valve rod is engaged into the communication path 21 in the liquid-tight relation thereto so that the communication between the water level adjusting chamber 20 and the vaporizing chamber 16 is interrupted. As the same time, the microswitch 50 is actuated by the actuating arm 49 of the rod 36 and the power supply circuit is turned on so that, with the plug 72 of the cord 71 connected to the commercial power source, the electric current is supplied to the heater means 24, the supplied current to the electrode plates 64 of the heater means 24 causes heat generated by the elements 63 to heat the plate 60, whereby water of the predetermined amount for the heat radiating plate 60 is boiled to fill the vaporizing chamber 16 with generated vapor, which is passed through the channel 59, outlet passage 54 and ejection pipe 55 to the nozzle 56 to be ejected thereout. The ejected vapor causes the Venturi action with respect to the suction nozzle 75 so that the salt solution or the like inhalant contained in the inhalant chamber 73 is sucked through the suction pipe 76 out of the suction nozzle 75 to be atomized with the ejected vapor from the nozzle 56 and discharged from the atomized vapor outlet 13 of the cover 14 into, for example, the user's mouth.

During the foregoing operation, as the amount of water supplied to the heater means 24 in the vaporizing chamber 16 is always kept substantially constant and the heat radiating plate 60 has the two continuous inverted U-shaped portions providing an increased surface area, the heat radiating plate 60 can have an effectively widened heating area for the predetermined amount of water, whereby required time for generating vapor after the operation of the push button 38 can be substantially always kept constant as effectively shortened. In other words, since it is required to boil only a relatively small amount of water which has been supplied in the vaporizing chamber 16, the vapor generating efficiency can be remarkably improved. As the communication between the vaporizing chamber 16 and the water level adjusting chamber 16 is interrupted by the closure of the communication path 21, further, any convection of water being heated toward the water supply chamber 19 can be prevented during the energization of the heater means 24, whereby the vapor generating efficiency can be additionally increased.

When the user releases his depression of the push button 38, on the other hand, the valve rod 36 returns to its upper position due to the returning force of the spring 48, the closure flange 40 which has been closing so far the vapor release vent 39 together with the closing by the tip end portion 23 of the communication path 21 is separated from the vapor release vent 39 and, simultaneously, the releasing of the tip end portion 23 from the communication path 21 and of the actuating arm 49 from the microswitch 50 is achieved. Any vapor remained in the vaporizing chamber 16 at this time is gradually discharged to the exterior of the front wall 15 through the vapor release path of the vent 39, space 51 and duct 53 which is rather winding than to be straight, rendering the vapor discharge velocity to be relatively slow, so that any risk of causing such vapor to be ejected from the atomized vapor outlet 13, top cover 14 or the like can be prevented to eliminate any possibility that the user gets burnt. Upon the upward shift of the valve rod 36 causing its arm 49 separated from the microswitch 50, further, the power supply circuit is turned off and the heater means 24 is deenergized so that, when the use of the inhalator is stopped, no continuous vapor ejection will occur. In addition, the upward shift of the valve rod 36 causes water to be soon supplied to the vaporizing chamber 16, so that the vaporizing chamber 16 can never become vacant and can be prevented from, for example, being heated without water.

What is claimed as my invention is:

1. An inhalator comprising:
a casing including
a housing, and
a cover mounted atop said housing and forming a vapor discharge port adjacent a front end of said casing,
a suction tank disposed in said casing at a front end thereof below said discharge port for containing an inhalant,
a suction tube extending into said suction tank and including a suction nozzle at its upper end,
a water supply chamber disposed in said casing for containing a supply of water,
a vaporizing chamber disposed in said casing forwardly of said supply chamber and including a portion disposed below said supply chamber,
said vaporizing chamber including a vapor release vent communicating said vaporizing chamber with a space disposed above said vaporizing chamber, said space communicating with the exterior of said casing,
a water level adjusting chamber disposed in said casing at about the same height as said vaporizing chamber and arranged to fluidly communicate said supply chamber with said vaporizing chamber,
said adjusting chamber communicating with said vaporizing chamber by means of a communicating path disposed below said vapor release vent,
said adjusting chamber including an air vent path communicating with said space,
valve means for closing said vent and said communicating path simultaneously,
a heater for heating and vaporizing water in said vaporizing chamber in response to the closing of said vent and communicating path by said valve means, and for terminating the heating of the water in response to the opening of said vent and communicating path, and
ejector means communicating with said vaporizing chamber for conducting vapor therefrom and ejecting the vapor toward said vapor discharge port and across said suction nozzle to create a Venturi effect for sucking inhalant from said suction tank and into the stream of vapor.

2. An inhalator according to claim 1, wherein said water supply chamber contains a water supply tank, said water supply chamber has in the bottom thereof a water supply port to which said water supply tank is coupled, said level of said water level adjusting and vaporizing chamber being lower than that of said water supply port so that the level of water in the adjusting and vaporizing chambers can be determined by the level of the water supply port.

3. An inhalator according to claim 1, which further comprises a winding path disposed above said vaporizing chamber in said casing and opened at one end to the exterior of the casing, said space above said vapor release vent being connected to the other end of said winding path.

4. An inhalator according to claim 1, which further comprises a power supply circuit for said heater, said valve means including an actuator which turns on said power supply circuit simultaneously with the closing of the valve means and turns off the circuit simultaneously with the opening of the valve means.

5. An inhalator according to claim 4, wherein said power supply circuit includes a microswitch disposed in the vicinity of said vapor release vent of said vaporizing chamber, said valve means comprises a push-button portion exposed out of said casing and a valve rod integral with said push-button portion for movement therewith upon depression of the push-button portion, and said valve rod is provided with a tip end engageable with said communication path, a closure flange engageable with said vapor release vent, and an extended arm constituting said actuator for turning on and off said microswitch of said power supply circuit.

* * * * *